(12) United States Patent
Engel et al.

(10) Patent No.: US 9,599,577 B2
(45) Date of Patent: Mar. 21, 2017

(54) X-RAY IMAGING WITH PIXELATED DETECTOR

(75) Inventors: Klaus Juergen Engel, Aachen (DE); Gereon Vogtmeier, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 252 days.

(21) Appl. No.: 13/818,696

(22) PCT Filed: Aug. 30, 2011

(86) PCT No.: PCT/IB2011/053784
§ 371 (c)(1),
(2), (4) Date: Feb. 25, 2013

(87) PCT Pub. No.: WO2012/032435
PCT Pub. Date: Mar. 15, 2012

(65) Prior Publication Data
US 2013/0156157 A1    Jun. 20, 2013

(30) Foreign Application Priority Data
Sep. 6, 2010  (EP) .................................. 10175358

(51) Int. Cl.
*G01N 23/04*    (2006.01)
*G21K 1/02*    (2006.01)

(52) U.S. Cl.
CPC ............ *G01N 23/04* (2013.01); *G21K 1/025* (2013.01); *G21K 2207/00* (2013.01); *H01J 2235/068* (2013.01)

(58) Field of Classification Search
CPC .... G21K 1/025; G21K 2207/00; G01N 23/04; G01N 23/046; H01J 2235/068
USPC .......................................................... 378/149
See application file for complete search history.

(56) References Cited

U.S. PATENT DOCUMENTS

| | | | |
|---|---|---|---|
| 4,315,157 A | 2/1982 | Barnes | |
| 5,245,191 A | 9/1993 | Barber et al. | |
| 5,461,653 A * | 10/1995 | Parker | G21K 1/025 378/155 |
| 5,802,137 A * | 9/1998 | Wilkins | 378/149 |
| 5,812,629 A * | 9/1998 | Clauser | A61B 6/032 378/37 |
| 6,064,718 A * | 5/2000 | Holland et al. | 378/122 |
| 6,343,110 B1 | 1/2002 | Li | |

(Continued)

FOREIGN PATENT DOCUMENTS

| | | |
|---|---|---|
| EP | 2197251 A1 * | 6/2010 |
| GB | 2035769 A | 6/1980 |

(Continued)

*Primary Examiner* — Glen Kao

(57) ABSTRACT

The invention relates to a method and an imaging system (100) for generating X-ray images. The system (100) comprises at least one X-ray source, preferably an array of X-ray sources (101a-101d), and an X-ray detector (103) with an array of sensitive pixels (103a-103e). A collimator (102) is arranged between the X-ray source and the detector such that two openings (P) of the collimator (102) allow the passage of X-rays towards two neighboring pixels (103a-103e) while the region between said pixels is substantially shielded. This shielding of the usually insensitive regions between pixels reduces unnecessary X-ray exposure. A sufficiently large X-ray intensity can be achieved by using a plurality of small X-ray sources (101a-101d).

20 Claims, 2 Drawing Sheets

(56) References Cited

U.S. PATENT DOCUMENTS

| | | | |
|---|---|---|---|
| 6,850,595 B2 | 2/2005 | Zhou et al. | |
| 6,895,079 B2 | 5/2005 | Birdwell et al. | |
| 7,209,545 B2 | 4/2007 | Radley et al. | |
| 8,306,184 B2 | 11/2012 | Chang et al. | |
| 2001/0048732 A1* | 12/2001 | Wilson et al. | 378/62 |
| 2002/0094064 A1 | 7/2002 | Zhou et al. | |
| 2003/0043958 A1* | 3/2003 | Mihara | A61B 6/032 378/4 |
| 2007/0009081 A1 | 1/2007 | Zhou et al. | |
| 2007/0133749 A1* | 6/2007 | Mazin et al. | 378/147 |
| 2008/0043920 A1* | 2/2008 | Liu et al. | 378/138 |
| 2012/0039446 A1* | 2/2012 | Cui et al. | 378/149 |

FOREIGN PATENT DOCUMENTS

| | | |
|---|---|---|
| JP | 2005261838 A | 9/2005 |
| WO | 95/12884 | 5/1995 |
| WO | 2010055930 A1 | 5/2010 |

* cited by examiner

X-RAY IMAGING WITH PIXELATED DETECTOR

FIELD OF THE INVENTION

The invention relates to a method and an imaging system for generating X-ray images with an X-ray source and an X-ray detector. Moreover, it relates to an X-ray generator for such an imaging system.

BACKGROUND OF THE INVENTION

From the WO 2010/0055930 A1, an X-ray imaging apparatus is known which comprises a plurality of X-ray sources, a collimator with a plurality of slits, and an X-ray detector with a plurality of detecting elements. Selective activation of an X-ray source and modification of the collimator geometry allows to vary the projection view without a physical movement of detector or X-ray source.

SUMMARY OF THE INVENTION

It was an object of the present invention to provide improved means for the X-ray imaging of an object with a pixelated detector, wherein it is particularly desirable to achieve a better exploitation of the X-ray dose the object is exposed to.

This object is achieved by an X-ray imaging system according to claim 1, a method according to claim 2, and an X-ray generator according to claim 11. Preferred embodiments are disclosed in the dependent claims.

According to a first aspect, the invention relates to an X-ray imaging system for generating X-ray images of an object, for example of a patient in a medical X-ray laboratory, or of a piece of luggage in a security system, wherein the X-ray detector has for technical reasons radiation insensitive areas between pixels inside the illuminated area. The generated images will in general consist of projections of the object, which may optionally be synthesized to sectional images by Computed Tomography (CT). The X-ray imaging system comprises the following components:

a) At least one X-ray source for generating an X-ray beam. In this context, the term "X-ray" shall in a broad sense comprise any high-energy electromagnetic radiation, typically radiation with a wavelength between about $10^{-8}$ and $10^{-12}$ m. The generated X-ray beam may in general have any geometry, consisting for example of (approximately) parallel X-rays. Most preferably, each X-ray source is however approximately point-like (in relation to the other components of the imaging system), yielding a fan-shaped or cone-shaped X-ray beam.

b) An X-ray detector that comprises an array of X-ray sensitive units or elements separated by X-ray insensitive regions between said units (i.e. regions that do not convert received radiation into useful measurement signals). As the detection signal of these units usually corresponds to image information at a particular point of the generated projection, these sensitive units will in the following as usual be called "pixels". The array comprises at least two of these pixels, typically however a large number of several thousands of pixels that are arranged in a one- or two-dimensional pattern. The X-ray detector is arranged in the field of view of the X-ray source such that the pixels can be reached by the generated X-ray beam.

c) A collimator that comprises at least two openings, wherein the geometry of X-ray source, X-ray detector, and collimator is such that the at least two openings allow the passage of X-rays from at least one X-ray source such that at least two neighboring pixels of the detector are illuminated while the radiation-insensitive region between said pixels is at least partially shielded from X-rays by the material of the collimator, i.e. it is illuminated with a weaker intensity. Typically, the intensity between the pixels is less than 75%, preferably less than 50%, most preferably less than 10% of the intensity within the pixels (when no object is present). The considered two openings are usually neighboring openings of the collimator.

d) An object space where an object to be imaged can be accommodated, said object space being located between the collimator and the X-ray detector.

According to a second aspect, the invention relates to a method for generating an X-ray image with an X-ray imaging system, particularly with an X-ray imaging system of the kind described above. The method comprises the following steps, which are typically executed simultaneously:

a) Generating an X-ray beam with at least one X-ray source.
b) Detecting X-rays of said beam at the positions of pixels of an array of pixels of an X-ray detector.
c) Allowing the passage of X-rays from said X-ray beam through at least two openings of a collimator such that at least two neighboring pixels of the detector are illuminated while the radiation-insensitive region between said pixel positions is at least partially shielded.
d) Accommodating an object to be imaged between the collimator and the detector.

In some X-ray imaging systems (as for example those commonly used in Computed Tomography), the region between two (neighboring) pixels of a pixelated X-ray detector is insensitive to X-radiation due to the design of the detector. Insensitive separation components may for example be located in these regions, or the regions may be occupied by an anti-scatter grid. X-rays that are directed towards such regions between two pixels will therefore not contribute to an image but only increase the dose an object is exposed to. Furthermore, such rays may even be counterproductive as they contribute to scattered radiation which compromises image quality. These negative effects are avoided in the imaging system and the method described above due to the collimator that shields the region between two pixels and that allows the passage of X-radiation only towards the sensitive pixel areas.

In the following, various preferred embodiments of the invention will be described that relate both to an imaging system and a method of the kind described above.

Thus the openings in the collimator may preferably be slits having an elongated geometry (e.g. with a rectangular shape) with a diameter in length-direction being several times larger than a diameter in the orthogonal width-direction. Preferably the slits may be such that they generate fan-shaped beams which illuminate a stripe on the pixel array extending from one border of the detector to the opposite.

In an alternative embodiment, the openings may be holes, i.e. they have a compact (e.g. circular, square or rectangular) shape. Most preferably, the holes have a shape that corresponds substantially to the shape of the pixels of the detector. In this case the complete X-ray sensitive area of one pixel can optimally be illuminated through such an opening with an adequate small source.

It was already mentioned that the pixel array of the X-ray detector will typically comprise (much) more than two radiation sensitive pixels. In a preferred embodiment, these pixels are aligned in a quasi-periodical array and, by means of the collimator, are illuminated with a higher intensity than radiation insensitive regions between them in at least one direction of (quasi-) periodicity of the array.

In general, a large multi-pixel sub-area of the detector can be illuminated by an X-ray source through one opening of the collimator. To optimize the shielding of insensitive regions between the pixels, it is however preferred that the size and arrangement of at least one opening of the collimator and of at least one X-ray source is such that substantially only one pixel or substantially only one row of pixels is illuminated through said opening. Most preferably, all openings of the collimator fulfill these conditions.

While the advantages of the invention can already be achieved with just two openings in the collimator, it is preferred that the collimator comprises an array typically having a higher number of openings which are one- or two-dimensionally aligned with the pixels of the detector. In this context, "alignment" of the openings with the pixels shall mean that any two neighboring openings allow the passage of X-rays towards two neighboring pixels while the region between said pixels is substantially shielded. To put it in other words, radiation from the X-ray source projects the openings of the collimator onto a pattern on the detector area that corresponds to (or preferentially is identical to) the pattern of pixels in this area.

The size (mean diameter) of the pixels of the X-ray detector typically ranges between about 0.1 mm and about 2 mm. Typical geometries of the pixels are rectangular, square, hexagonal, or any other shape that allows for a smart tiling of a one- or two-dimensional area.

The pitch of the pixels, i.e. the mean distance between two characteristic points (e.g. the centers) of neighboring pixels, preferably ranges between about 0.5 mm and 2 mm. The pitch of the pixels contributes to the image resolution that can be achieved with the imaging system for a given size and arrangement of the X-ray source.

The width of the openings of the collimator preferably ranges between about 100 μm and 500 μm. For noncircular openings, said width is defined as the diameter of the largest circle which can completely be inscribed in the opening.

The pitch of the openings of the collimator preferably ranges between about 100 μm and 500 μm.

The advantages of the present invention can in principle be achieved with just a single X-ray source. As a real X-ray source has however some finite spatial extension, the illumination of the pixels through the openings of the collimator will necessarily be somewhat blurred due to penumbra effects. Limitation of such effects requires that the X-ray source should be as small as possible, which reduces however also the available intensity of the X-ray illumination. A solution to this dilemma is achieved if the imaging system comprises an "X-ray generator" with a plurality of X-ray sources that fulfill the conditions of the invention, i.e. for each X-ray source there are at least two openings of the collimator which allow the passage of X-rays towards two neighboring pixels while the region between said pixels is substantially shielded from radiation of the considered X-ray source. It is preferred that all X-ray sources are arranged within an area which is limited by a maximal diameter such that the spatial resolution of the image of the examined object is kept within a preferred specification. Typically this means that said area has a maximum diameter which corresponds to the diameter of the emission area of a focal spot of commonly used X-ray sources. On the other hand it is preferred that the X-ray sources are not as close together that they illuminate a pixel through the same collimator opening, as this would increase the effective beam penumbra per opening and thus have no benefit compared to the use of a single focal spot with extended emission area. Considering said arguments it is most preferred that the X-ray sources are aligned to the collimator openings in a way, that each X-ray source uses a different collimator opening for the illumination of a particular pixel or pixel set, thus implying that the X-ray sources keep some minimum distance from each other. By using a plurality of X-ray sources, the available intensity of radiation can be increased accordingly without increasing blurring effects.

In the aforementioned embodiment, there is preferably at least one pixel that is simultaneously illuminated by radiation passing through at least two different openings (said radiation coming from different X-ray sources).

According to a further development of the aforementioned embodiment, the geometry of the imaging system is chosen such that any two X-ray sources of the X-ray generator illuminate the same set of pixels through the openings of the collimator. Most preferentially, one can align all X-ray sources and all collimator openings quasi-periodically in a way that each individual X-ray source illuminates the detector array through the collimator openings with a pattern for which the X-ray sensitive pixel regions are illuminated with a higher intensity than the insensitive regions between the pixels. The illumination patterns of all X-ray sources then superpose to build a total illumination pattern which again fulfills the condition that X-ray sensitive pixel regions are illuminated with a higher intensity than the insensitive regions between the pixels. In an idealized case, each X-ray source illuminates all detector pixels, or, in an equivalent formulation, each detector pixel is illuminated simultaneously by all available X-ray sources.

Preferably the total size of the area containing the plurality of X-ray sources of the X-ray generator is comparatively small, so that—within the resolution limits of the detector—the projections through an object generated from all the X-ray sources are substantially the same. As already said, the total area covered by the X-ray sources is preferably comparable to the size of focal spots in conventional X-ray tubes. Most preferably, the plurality of all X-ray sources covers an area of less than about 10 $mm^2$. The (maximal) diameter of the individual X-ray sources of the X-ray generator is typically smaller than 100 μm, preferably smaller than 50 μm.

According to a third aspect, the invention relates to an X-ray generator for an imaging system of the kind described above, said generator comprising a plurality of X-ray sources. The X-ray generator is characterized in that it comprises an emission area with modulated emission intensity. Peaks of emission intensity will then functionally constitute different X-ray sources.

In a first preferred embodiment of the X-ray generator, said generator comprises electron optics and/or a structured electron emitter for bombarding the emission area with electrons in a pattern that generates an array of emission peaks. While in conventional X-ray tubes the focal spot on the target is uniformly bombarded with electrons, the present invention creates some micro-structure in the target area with a plurality of emission peaks.

The aforementioned structured electron emitter may preferably be structured in a pattern that is a scaled copy of the pattern of the X-ray source array. In this case only a simple linear "optical" imaging of the emitted electrons onto the emission area is required.

An electron emitter with a sufficiently fine structure may particularly be realized by carbon nanotube emitters. More information on carbon nanotubes and X-ray sources that can be built with them can for example be found in the U.S. 2002/0094064 A1 or U.S. Pat. No. 6,850,595.

According to another embodiment, the X-ray generator comprises a spatially extended X-ray emitter that is disposed behind a mask with holes. The extended X-ray emitter can for example be the focal spot of a conventional X-ray tube, having a size of typically several square millimeters. The holes of the mask will function in this embodiment as the required multitude of point-like X-ray sources.

BRIEF DESCRIPTION OF THE DRAWINGS

These and other aspects of the invention will be apparent from and elucidated with reference to the embodiment(s) described hereinafter. These embodiments will be described by way of example with the help of the accompanying drawings in which.

Like reference numbers or numbers differing by integer multiples of 100 refer in the Figures to identical or similar components.

DESCRIPTION OF PREFERRED EMBODIMENTS

In many conventional X-ray imaging modalities (especially in CT), the X-ray detector has inactive regions characterized as gaps between pixels. For a CT detector, the gaps are currently unavoidable as they are necessarily used for the absorption lamellae of an anti-scatter collimator (also known as anti-scatter-grid). During operation, the X-ray cone beam also illuminates the inactive detector areas. This results in an unnecessary dose exposure to the patient.

In view of this, a method is suggested here which allows to spatially modulate the X-ray cone beam such that the active detector areas (pixels) are almost fully illuminated and the inactive gaps between the pixels are at least less intense illuminated. Basically, the suggested method applies a multitude of needle beams instead of a more or less homogeneous illuminating cone beam.

Figure 1:
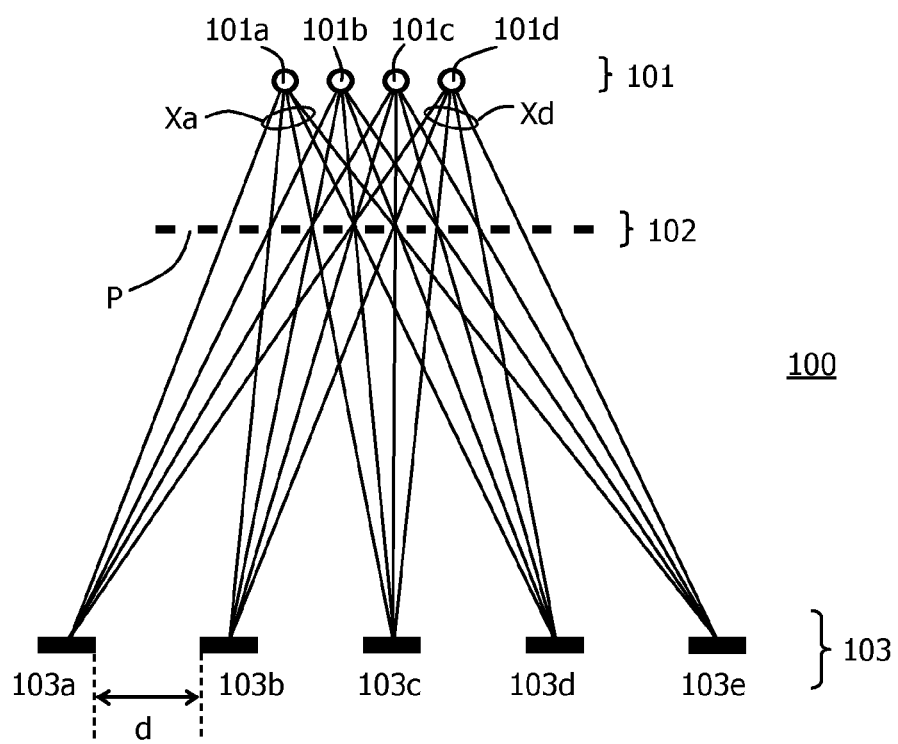
FIG. 1 schematically sketches the imaging geometry of a first imaging system according to the present invention having a plurality of single X-ray sources.

FIG. 1 schematically shows a side view of an imaging system 100 according to a first embodiment of the aforementioned concepts. The imaging system 100 comprises the following components:

an X-ray generator 101 with an array of separate X-ray sources 101a, . . . 101d for generating X-ray beams Xa, . . . Xd;

a collimator 102 with pin-holes P;

an X-ray detector 103 with a (one- or two-dimensional) array of sensitive pixels 103a, . . . 103e.

An object to be imaged (not shown) may be disposed in the "object space" between the collimator 102 and the detector 103.

The basic idea of the imaging system 100 is to use the pin-hole mask 102 as a collimator to create an array of needle beams, each beam reaching exactly one of the pixels 103a, . . . 103e. The pin-hole collimator 102 works already excellent with a single X-ray source (e.g. source 101a), if an ideal point-like X-ray source is (would be) used.

For an X-ray source spot size of typically (effective, e.g. as seen by the detector) 0.5 mm×1 mm, however, one can easily prove that such a spatially extended source creates a penumbra, which in practical cases (source-detector distance of 1 m and source-collimator distance of 20 cm) has a width of at least 2 mm. Compared to typical detector pixel pitches of about 1.2 mm this is too broad.

Figure 2:
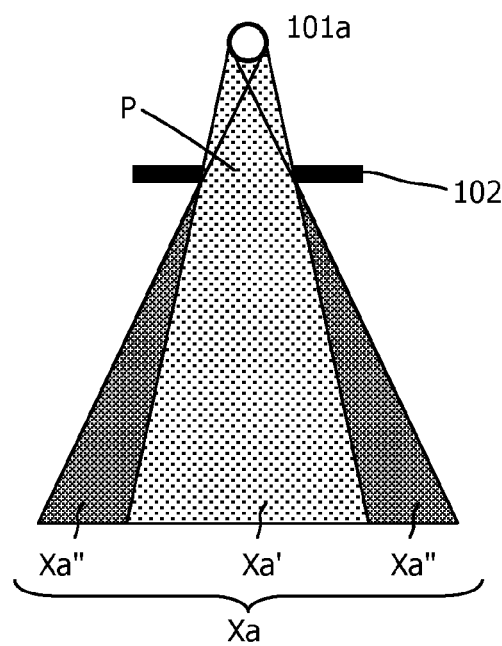
FIG. 2 shows in detail the optics at a single collimator opening.

To decrease the needle beam extension, two actions must be taken: Firstly, the focal spot size must be decreased. Secondly, the pin-holes P of the collimator 102 must be decreased in size. To create a needle beam extension of 1 mm full-width-half-maximum (FWHM) at the detector 103 with 200 µm wide gaps d between pixels, for the above mentioned distances a pin-hole collimator 102 with a pitch of 240 µm and a hole size of 200 µm has to be used. To ensure an adequate small penumbra of 200 µm width, a single focal spot has to be reduced to a size of 50 µm. FIG. 2 illustrates the resulting ray geometry for a single X-ray source 101a and a single pin-hole P of the collimator 102, allowing the passage of a central beam Xa' with a penumbra Xa''.

A single focal spot of the aforementioned size is likely to suffer from too low total intensity. It is therefore preferred to use not only one small source, but an array of several small X-ray sources 101a, . . . 101d. Preferably, the total area including these small X-ray sources 101a, . . . 101d corresponds to common focal spot sizes. Moreover, the pitch of the small X-ray sources 101a, . . . 101d is adapted such that the projected image of the source array on the detector 103 fits the pixel pitch (i.e., for 1.2 mm detector pixel pitch, the source array would require a pitch of about 300 µm). The fine-structured X-ray generator 101 thus provides an array of very small focal spots, which assures that a multitude of needle beams get sharp enough to illuminate only the active pixel regions.

Practically, the array of X-ray sources 101a-101d could be realized with the help of electron optics similar to those already used in common X-ray tubes; however, the electron emitter has to be structured such that electrons are emitted only in those areas which correspond to a scaled copy of the X-ray source array. This is feasible for example with structured carbon nanotube emitters.

The pin-hole mask of the collimator 102 can be fabricated as an etched metal foil which is added into the path of rays somewhere in front of the object (not shown). Potentially the collimator 102 can be combined with common pre-filtering or beam shapers. It has to be taken into account that the distance between the collimator 102 and the X-ray generator 101 as well as the local hole pitch of the collimator must be always adapted such that the projected image of each of the X-ray sources 101a, . . . 101d fits the detector pixel pitch.

Figure 3:
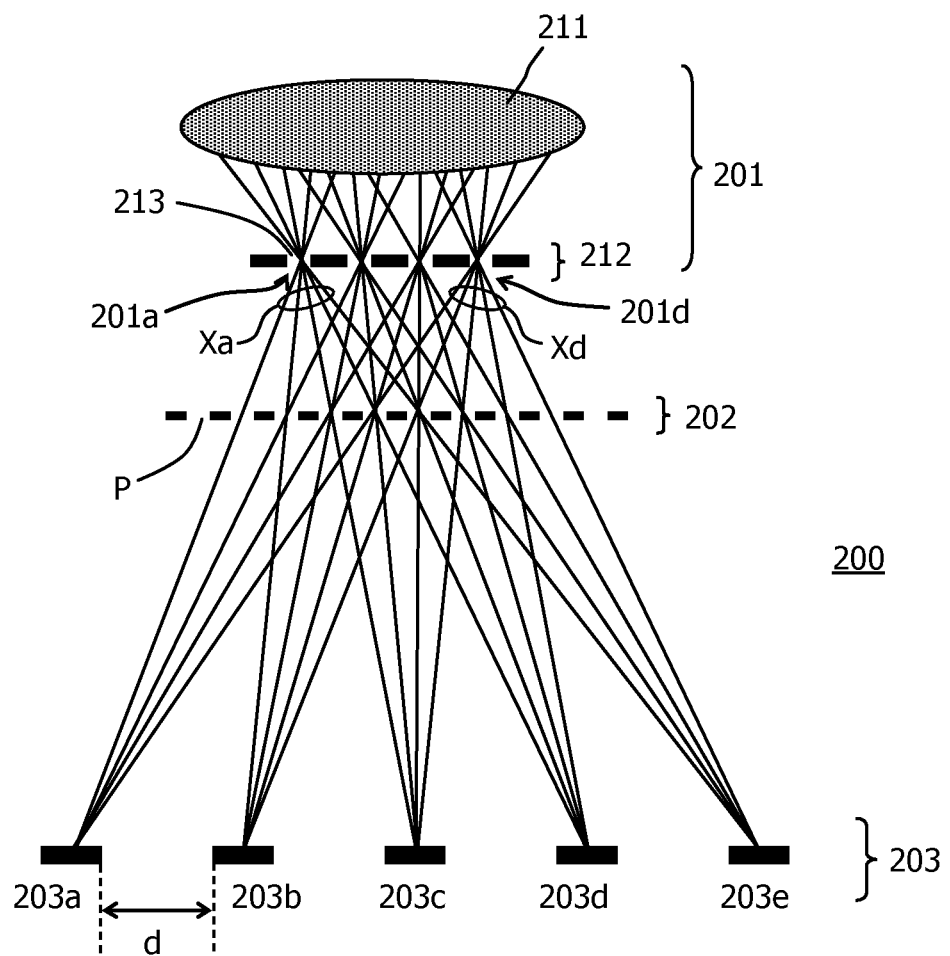
FIG. 3 schematically sketches the imaging geometry of a second imaging system according to the present invention in which an extended X-ray emitter with a mask is used to generate a plurality of X-ray sources.

FIG. 3 shows a second embodiment of an imaging system 200 with an X-ray generator 201 which allows the use of a common X-ray tube with a single focal spot 211 (optionally with dual or quattro focal spot technology). This approach can be implemented with reasonable effort into already available CT scanners.

The focal spot 211 of a common X-ray tube (not shown in detail) is pre-patient collimated by a (second) mask 212 or grating with pinholes 213. Basically, the indicated point sources shown in FIG. 1 are replaced by openings 213 of the second mask 212, while the X-ray focal spot 211 needs not to be structured any more.

As seen in FIG. 3, the pitch of the mask 212 is larger than that of the collimator 202, therefore this mask 212 is even easier to produce than the collimator 202.

The optimal structure of the grating 212 depends on whether one wants to create a set of fan beams (useful in case that the detector pixel gaps are negligible small in one direction), or a set of needle beams (useful for common CT detectors having pixel arrays with inactive gaps in each direction). For the fan beam case, one has to produce line gratings, while for the second case one has to produce masks with rectangular openings.

It is an advantage of the present invention that the total exposure to a patient is reduced by the part of X-rays absorbed by the pin-hole collimator, but without loss of image quality, ideally even with maintaining the tube intensity received per active pixel area in absence of a pin-hole collimator. As a positive side effect, less X-ray scattered radiation is generated, leading to an improvement of the image quality. The invention can be applied especially with X-ray Computed Tomography systems, but also more generally to all X-ray imaging systems characterized by inactive areas between detector pixels.

Finally it is pointed out that in the present application the term "comprising" does not exclude other elements or steps, that "a" or "an" does not exclude a plurality, and that a single processor or other unit may fulfill the functions of several means. The invention resides in each and every novel characteristic feature and each and every combination of characteristic features. Moreover, reference signs in the claims shall not be construed as limiting their scope.

The invention claimed is:

1. An X-ray imaging system for generating X-ray projections of an object, comprising:
    a plurality of X-ray sources for generating an X-ray beam;
    a stationary single integrated X-ray detector that comprises an array of at least two sensitive pixels having X-ray insensitive regions in between, wherein a detection signal of these pixels corresponds to image information at a particular point of the generated projection;
    a stationary collimator that comprises at least two openings which allow the passage of X-rays from the plurality of X-ray sources such that each of at least two neighboring pixels of the single integrated X-ray detector is illuminated by X-rays passing through both of the at least two openings while the X-ray insensitive region between said pixels is at least partially shielded by the collimator;
    an object space between the collimator and the X-ray detector where an object to be imaged can be accommodated, wherein the stationary collimator is disposed between the plurality of X-ray sources and the object space.

2. The X-ray imaging system according to claim 1, wherein a size and an arrangement of one opening of the at least two openings and one X-ray source of the plurality of X-ray sources are such that only one pixel of the array of the at least two sensitive pixels is illuminated through said one opening by said one X-ray source.

3. The X-ray imaging system according to claim 2, wherein X-rays from at least two of the plurality of X-ray sources traverse through a same opening of the at least two openings and illuminates two different pixels.

4. The X-ray imaging system according to claim 1, wherein the collimator comprises an array of openings which are in one dimension or in two dimensions aligned with the pixels of the detector such that by illumination with the plurality of X-ray sources, areas of the radiation sensitive pixels are illuminated with a higher intensity than the radiation insensitive regions between them in at least one direction of the pixel array.

5. The X-ray imaging system according to claim 1, wherein a size of the pixels ranges between about 0.1 mm and about 2 mm and/or a pitch of the pixels ranges between about 0.5 mm and 2 mm.

6. The X-ray imaging system according to claim 1, wherein a width of the openings of the collimator ranges between about 100 µm and 500 µm, and/or a pitch of the openings of the collimator ranges between about 100 µm and 500 µm.

7. The X-ray imaging system according to claim 1, wherein a size and an arrangement of each opening of the at least two openings and each X-ray source of the plurality of X-ray sources is such that one pixel of the array of the at least two sensitive pixels is illuminated by X-rays passing through all of the at least two openings from all of the X-ray sources.

8. The X-ray imaging system according to claim 1, further comprising:
    an X-ray generator with the plurality of X-ray sources, wherein any two of the plurality of X-ray sources is arranged to illuminate a same set of pixels through the openings of the collimator such that an area of the radiation sensitive pixels is illuminated with a higher intensity than the radiation insensitive regions between them in at least one direction of the pixel array.

9. The X-ray imaging system according to claim 8, wherein the plurality of X-ray sources and the collimator openings are arranged in a quasi-periodical pattern.

10. The X-ray imaging system according to claim 1, further comprising:
    an X-ray generator with the plurality of X-ray sources, wherein the plurality of X-ray sources covers an area of less than about 10 mm$^2$.

11. The X-ray imaging system according to claim 1, further comprising:
    an X-ray generator with the plurality of X-ray sources, wherein the X-ray generator comprises an emission area with modulated emission intensity.

12. The X-ray imaging system according to claim 11, wherein the X-ray generator comprises electron optics and/or a structured electron emitter for bombarding the emission area with electrons in a pattern that generates an array of emission peaks.

13. The X-ray imaging system according to claim 12, wherein the electron emitter is structured in a pattern corresponding to the pattern of the X-ray source array.

14. The X-ray imaging system according to claim 12, wherein the electron emitter comprises carbon nanotubes.

15. The X-ray imaging system according to claim 11, wherein the X-ray generator comprises a spatially extended X-ray emitter disposed behind a mask with holes.

16. The X-ray imaging system of claim 1, wherein a diameter of an individual X-ray source is less than one hundred microns.

17. The X-ray imaging system of claim 1, wherein a diameter of an individual X-ray source is less than fifty microns.

18. The X-ray imaging system of claim 1, wherein the plurality of all X-ray sources covers an area of less than ten square millimeters.

19. The X-ray imaging system of claim 1, and further comprising:
an X-ray absorbing grating with a plurality of pinholes,
wherein the X-ray absorbing grating is disposed between at least one of the plurality of X-ray sources and the collimator,
wherein X-ray radiation emitted by the single X-ray source is absorbed by the X-ray absorbing grating and traverses the plurality of pinholes, providing a plurality of X-ray sub-sources, and
wherein the collimator allows the passage of the X-rays emitted by the X-ray sub-sources such that the at least two neighboring pixels of the detector are illuminated and at least partially shields the X-ray insensitive region from the X-rays emitted by the X-ray sub-sources.

20. A method for generating an X-ray projection with an X-ray imaging system, said method comprising the following steps:
generating an X-ray beam with a plurality of X-ray sources;
detecting X-rays of said beam at positions of pixels of an array of pixels of a stationary single integrated X-ray detector having X-ray insensitive regions in between, wherein a detection signal of these pixels corresponds to image information at a particular point of the generated projection;
allowing passage of X-rays of said X-ray beam through two openings of a stationary pre-object collimator such that at least two neighboring pixels of the single integrated X-ray detector are each illuminated by X-rays passing through both of the two openings while the X-ray insensitive region between said pixels is at least partially shielded by the collimator;
d) accommodating an object to be imaged between the collimator and the detector.

\* \* \* \* \*